(12) United States Patent
Escoffier

(10) Patent No.: US 11,742,103 B2
(45) Date of Patent: Aug. 29, 2023

(54) DIAPHRAGM-LIKE PROTECTION FOR EQUIPPING A SHEATH LINING A PASSAGE THROUGH A WALL

(71) Applicant: ORANO DS—DÉMANTÈLEMENT ET SERVICES, Gif sur Yvette (FR)

(72) Inventor: Cédric Escoffier, Bagnols sur Ceze (FR)

(73) Assignee: ORANO DS—DÉMANTÈLEMENT ET SERVICES, Gif sur Yvette (FR)

( * ) Notice: Subject to any disclaimer, the term of this patent is extended or adjusted under 35 U.S.C. 154(b) by 157 days.

(21) Appl. No.: 16/623,242

(22) PCT Filed: Jun. 19, 2018

(86) PCT No.: PCT/FR2018/051465
§ 371 (c)(1),
(2) Date: Dec. 16, 2019

(87) PCT Pub. No.: WO2018/234683
PCT Pub. Date: Dec. 27, 2018

(65) Prior Publication Data
US 2021/0142924 A1 May 13, 2021

(30) Foreign Application Priority Data
Jun. 20, 2017 (FR) ........................................ 1755626

(51) Int. Cl.
*A61B 6/06* (2006.01)
*G21F 7/005* (2006.01)
(Continued)

(52) U.S. Cl.
CPC ................ *G21F 7/005* (2013.01); *A61B 6/06* (2013.01); *G21C 11/026* (2013.01); *G21C 11/028* (2013.01); *G21F 3/00* (2013.01)

(58) Field of Classification Search
CPC ......... G21F 7/005; G21F 3/00; G21C 11/026; G21C 11/028; A61B 6/06
(Continued)

(56) References Cited

U.S. PATENT DOCUMENTS 4,450,578 A * 5/1984 Hill ........................... G21F 5/04
378/150
2005/0173658 A1 8/2005 Lemer
(Continued)

FOREIGN PATENT DOCUMENTS

JP 2005523437 A 8/2005
JP 2008539833 A 11/2008
(Continued)

OTHER PUBLICATIONS

International Search Report for PCT/FR2018/051465 dated Nov. 6, 2018.
(Continued)

*Primary Examiner* — Kiet T Nguyen
(74) *Attorney, Agent, or Firm* — Pearne & Gordon LLP

(57) ABSTRACT

A biological protection for closing an opening in a wall delimiting a radiation zone, this protection comprising at least one iris diaphragm with a base in the form of a flat disk carrying petals formed by plates having a triangular contour and made of a material protecting against ionising radiation. These petals are movable parallel to the base between an open state in which the petals delimit together a central aperture and a closed state in which the petals are closely joined to form together a continuous closed wall.

12 Claims, 6 Drawing Sheets

(51) Int. Cl.
*G21C 11/02* (2006.01)
*G21F 3/00* (2006.01)

(58) Field of Classification Search
USPC ..................................... 250/505.1; 378/152
See application file for complete search history.

(56) References Cited

U.S. PATENT DOCUMENTS

2009/0074148 A1    3/2009  Echner
2013/0294583 A1*  11/2013  Tanabe .................... G21K 1/04
                                                          378/152
2019/0125283 A1    5/2019  Melman et al.

FOREIGN PATENT DOCUMENTS

JP    2017502274 A    1/2017
WO    2017222559 A1  12/2017

OTHER PUBLICATIONS

Written Opinion for PCT/FR2018/051465 dated Nov. 6, 2018.
Search Report for French application No. FR1755626 dated Mar. 19, 2018.
Translation of the Office action issued by the Korean Intellectual Property Office dated Dec. 15, 2022 for application 10-2019-7037470.
English translation of the Office action dated Feb. 6, 2023 for Chinese application No. 201880041077.x.

* cited by examiner

DIAPHRAGM-LIKE PROTECTION FOR EQUIPPING A SHEATH LINING A PASSAGE THROUGH A WALL

CROSS-REFERENCE TO RELATED APPLICATIONS

This is a National Stage application of PCT international application PCT/FR2018/051465, filed on Jun. 19, 2018, which claims the priority of French Patent Application No. 17 55626, filed Jun. 20, 2017, both of which are incorporated herein by reference in their entireties.

TECHNICAL FIELD

The invention relates to the field of the biological protections used in a nuclear power station to protect from ionising radiation.

PRIOR ART

In order to carry out investigative, measurement or other operations in a zone producing ionising radiation which is delimited by an enclosure, a pole is used, which is engaged in a sheath passing through a wall forming the enclosure.

In a tangible manner, an operator engages the pole in this sheath, the end of which pole is equipped, for example, with measuring equipment, and once the measurements are complete, the operator intervenes again and removes the pole from the sheath. The end of the pole can be equipped with other types of equipment, for example such as tooling for taking a sample or investigative equipment.

The problem that is posed by the use of such sheaths is that the operator is exposed to the ionising radiation, in particular since, when inserting or removing the pole, the operator may be located in the vicinity of the axis of the sheath, and thus be exposed to a direct flow of ionising radiation. In a more general manner, radiation can propagate outside of the protected zone by reflections between the sheath and the pole.

In this context, the sheath can, prior to the operation, be equipped with a biological protection made of material that protects from ionising radiation and having a central opening of a lesser diameter than that of the sheath.

This solution suffers from the drawback of having a single diameter of passage, whereas poles can have different diameters less than that of the opening of such a protection. This can be overcome by providing protections having openings of different diameters, which thus multiplies on-site handling operations to the same degree, since the sheath must be equipped with the protection suited to the diameter of the pole used.

Moreover, such biological protections are formed by assemblies of plates, most often made of lead, such that they can have a mass of several tens of kilograms. Moreover, this assembly of biological protection plates extends the sheath, hindering the manoeuvring of the pole.

Similarly, when switching over to safety mode, in particular at the end of a shift or at the end of the week, the sheaths are covered with biological protections which obstruct them completely to ensure that no radiation can propagate outside of the enclosure, which involves an equal number of additional handling operations.

In general, the handling of these biological protections is both tedious and hazardous for the operators as a result of the heavy weight thereof, and owing to the fact that access to the sheaths is not necessarily simple. This is accentuated further by the fact that the operators wear restrictive protective equipment on site.

Finally, this solution further involves, for each tool used, the design and manufacture of a suitable biological protection specific thereto, which results in high costs.

The purpose of the invention is to provide a solution that overcomes these drawbacks.

DESCRIPTION OF THE INVENTION

The invention relates to a biological protection for closing an opening in a containment wall of a radioactive zone, this protection comprising an iris-type diaphragm including a base in the form of a flat disc supporting petals formed by plates having substantially triangular contours and made of at least one material protecting from ionising radiation, which petals are capable of being displaced parallel to the base between an open state in which these petals jointly delimit a central opening and a closed state in which these petals are brought together to jointly form a continuous closed wall.

With this arrangement, the protection can be permanently installed on the sheath and can be opened to the appropriate diameter for the pole used, without requiring additional handling operations. Once the investigative operation is complete, the operator must simply manoeuvre the diaphragm to close the sheath without any other form of handling operation.

The invention further relates to a protection thus defined, wherein the petals are formed by a housing manufactured by additive manufacturing and into which the material protecting from ionising radiation is inserted.

The invention further relates to a protection thus defined, comprising means for guiding in translation each petal relative to the base, each petal being guided in a direction of translational displacement that is specific thereto, each direction of displacement of a petal forming a certain angle relative to this petal, this angle being identical for each petal.

The invention further relates to a protection thus defined, wherein each petal supports ball bearings in order to limit the friction forces generated between the petals and the base during the displacement of these petals.

The invention further relates to a protection thus defined, including a cover having a central opening, this cover covering all or part of the set of petals while being fastened to the base.

The invention further relates to a protection thus defined, wherein each petal supports ball bearings in order to limit the friction forces generated between the petals and the cover during the displacement of these petals.

The invention further relates to a protection thus defined, wherein the guide means are constituted by guideways formed in the cover and/or in the base, each guideway constituting a bearing track receiving one or more ball bearings of the petal guided thereby.

The invention further relates to a protection thus defined, wherein the different petals are identical, each petal having a substantially triangular shape, comprising a first edge and a second edge, and wherein all of the adjacent petals extend alongside one another by the first and second respective edges thereof, for any opening position of the diaphragm.

The invention further relates to a protection thus defined, wherein the first edge has a domed profile, in other words a convex profile, and wherein the second edge of each petal has a hollow profile, in other words a concave profile, that complements the profile of the first edge.

The invention further relates to a protection thus defined, wherein each petal has a substantially triangular contour having a bevelled apex, in order to limit the external overall dimensions of the protection in a maximally-open state.

The invention further relates to a protection thus defined, including a manoeuvring wheel mounted such that it can rotate relative to the cover and including, for each petal, a drive finger engaging within a corresponding groove of the corresponding petal in order to jointly displace all of the petals by rotating the wheel.

The invention further relates to a protection thus defined, wherein the wheel includes at least one manoeuvring stud passing through an arched slot formed in the cover, allowing this wheel to be rotated by displacing the stud along this slot in order to manoeuvre the protection between the open state thereof and the closed state thereof.

The invention further relates to a protection thus defined, including a transmission wheel mounted such that it can rotate relative to the base and including drive fingers that can engage within a groove of a corresponding petal, this transmission wheel including at least one transmission hole capable of receiving a drive stud of a drive wheel of another protection on which this protection is mounted, through at least one arched slot formed in the base.

The invention further relates to a biological protection system including a first protection and at least one second protection mounted on the first protection.

DETAILED DESCRIPTION OF SPECIFIC EMBODIMENTS

The idea on which the invention is founded is that of providing a protection in the form of a diaphragm capable of being opened to different diameters, and which is intended to permanently remain in place on the sheath equipped therewith.

Figure 1:
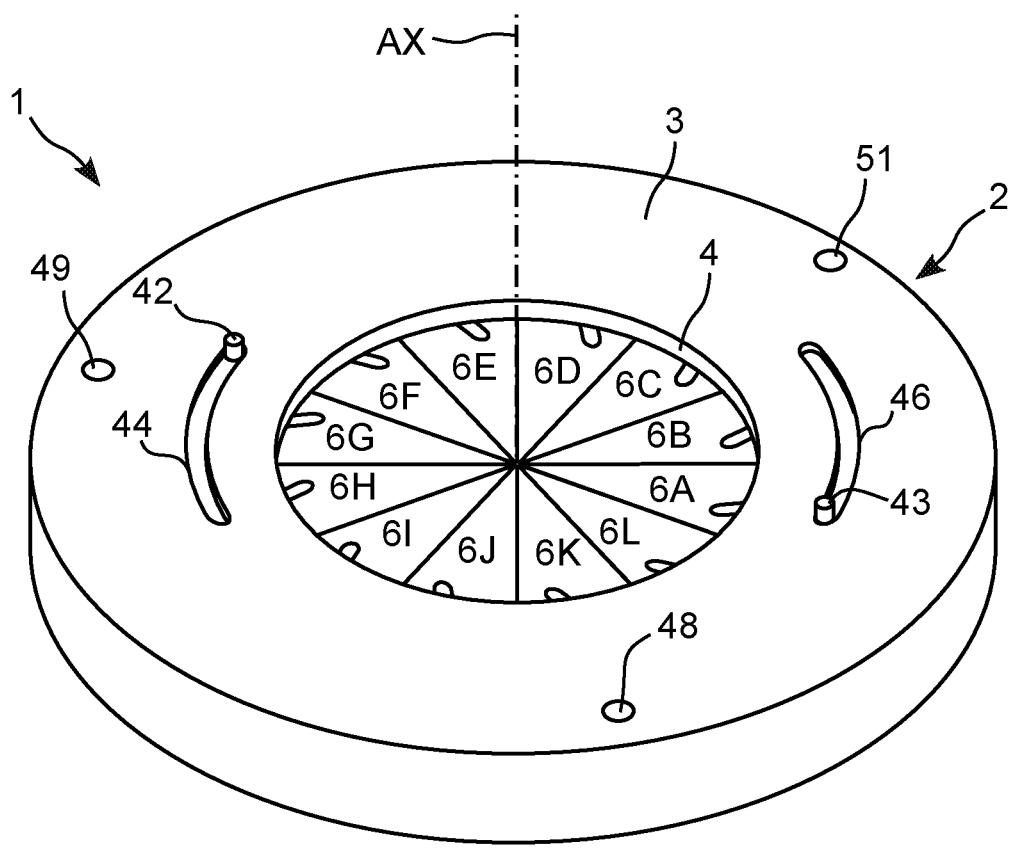
FIG. 1 is a perspective view of the diaphragm according to the invention in the closed state thereof.

As shown in FIG. 1, the protection according to the invention, denoted by the reference numeral 1, has a diaphragm architecture with an overall axisymmetric shape about an axis AX, delimited by a cover 2 having a flat top wall 3 including a central opening 4 that is closed by a set of petals in the situation shown in FIG. 1.

Figure 2:
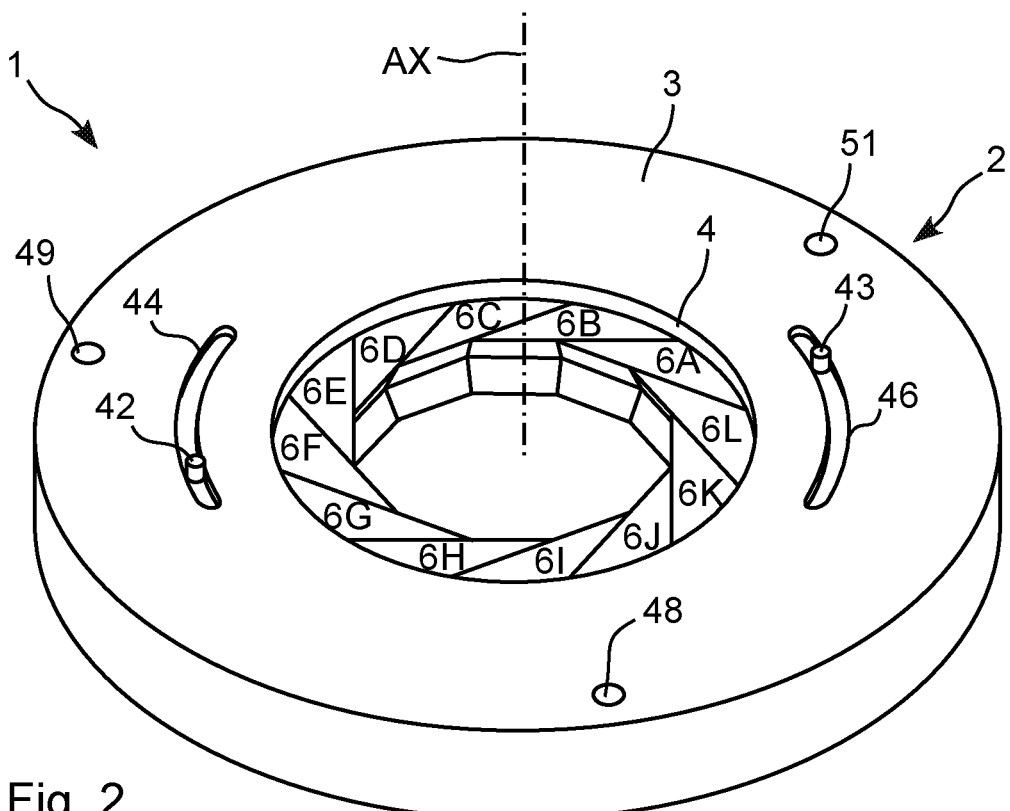
FIG. 2 is a perspective view of the diaphragm according to the invention when it is partially open.

These petals are capable of moving so as to move away from the central axis AX in order to open the diaphragm, for example in a partial manner as shown in FIG. 2, so as to allow a pole or other equipment to be engaged through the central opening 4.

These petals can also move away from the central axis in a maximal manner so as to entirely clear the central opening 4.

Figure 3:
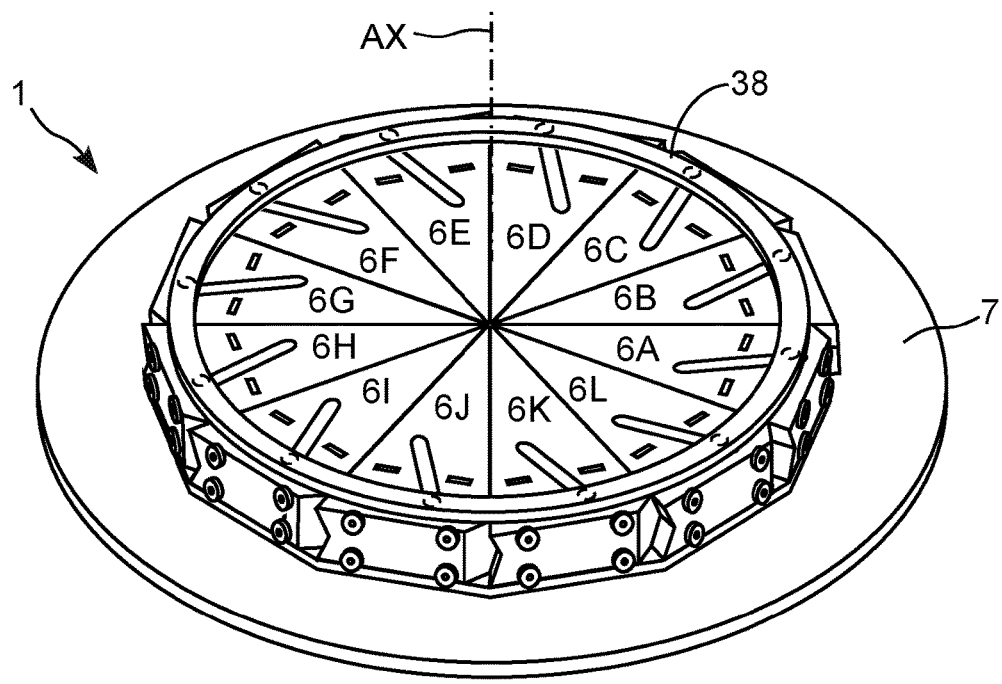
FIG. 3 is a perspective view of the diaphragm according to the invention without the cover thereof, showing the petals thereof when it is in the closed state.
Figure 4:
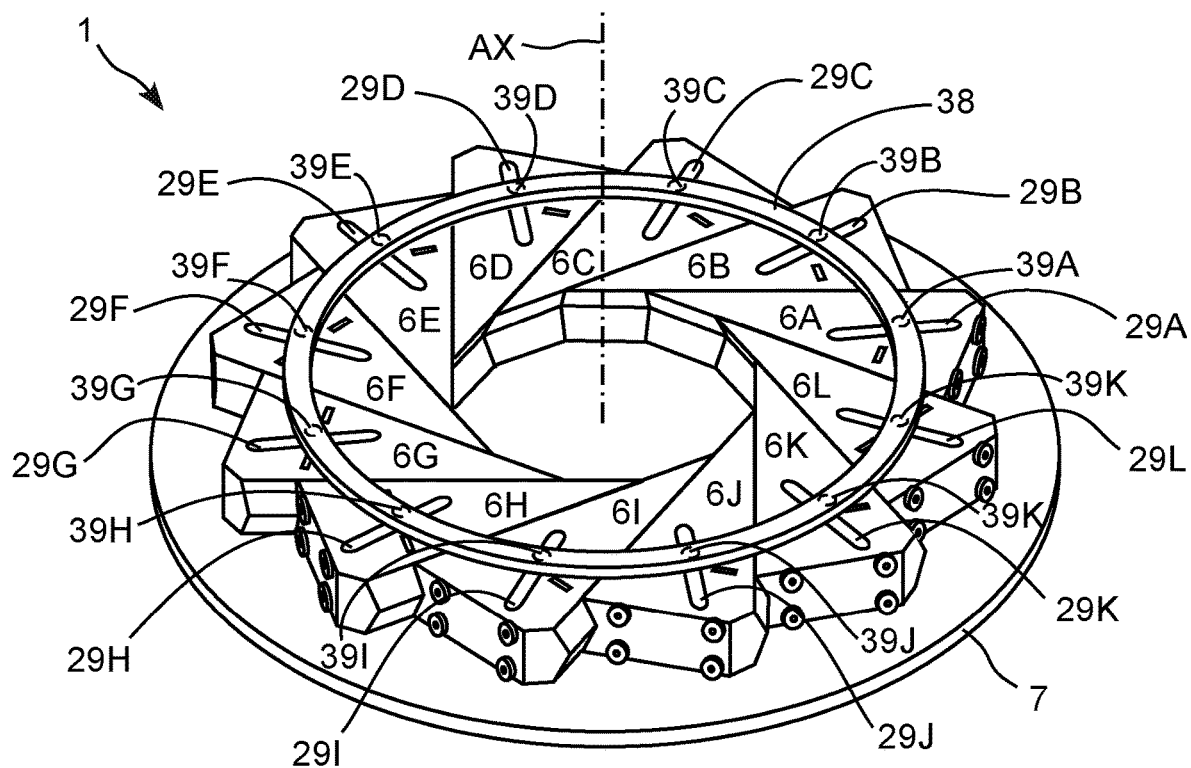
FIG. 4 is a perspective view of the diaphragm according to the invention without the cover thereof, showing the petals thereof when it is in the partially open state.

In the example shown in the figures, the diaphragm includes twelve identical petals, denoted by the reference numerals 6A to 6L, which are supported by a base 7 visible in FIGS. 3 and 4, which is generally flat in the shape of a disc centred about the axis AX and including a central opening perpendicular to the opening 4 of the cover.

The different petals are capable of undergoing joint translational displacement, each in a direction specific thereto, so as to be brought back towards the axis AX and close the opening as shown in FIG. 3, or so as to be moved away from the central axis AX to clear the opening as shown in FIG. 4.

Each petal is a flat plate manufactured from at least one material that protects from ionising radiation such as lead for example.

According to an alternative embodiment, the petals are constituted by a housing manufactured by additive manufacturing into which the material protecting from ionising radiation is inserted, for example by pouring. According to this alternative embodiment, the housing is made of a material that is not necessarily a material that protects from ionising radiation, but from a material that procures the strength—in particular the mechanical strength—required for the biological protection of the invention, for example steel.

Figure 6:
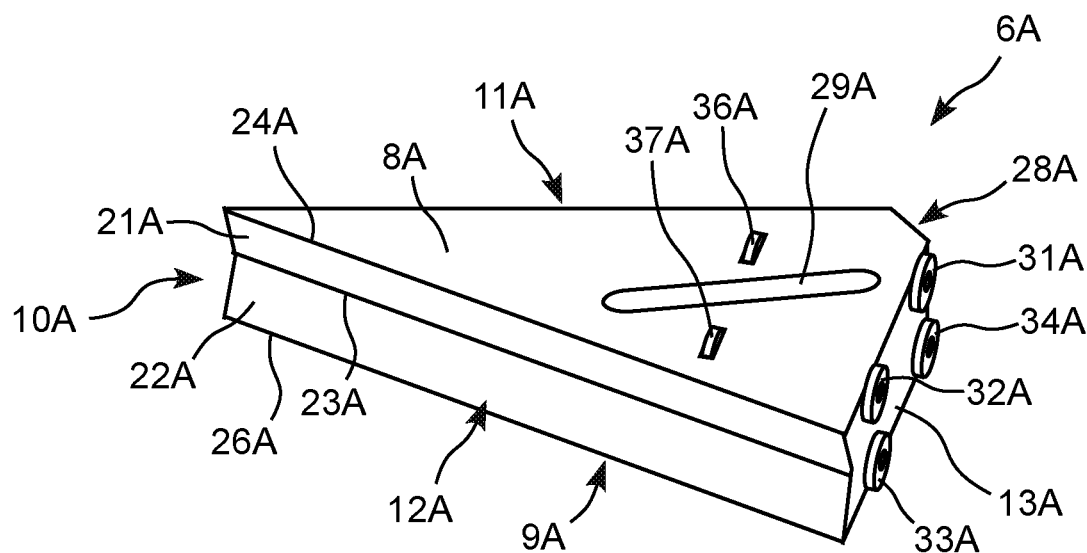
FIG. 6 is a second perspective view of a petal of the diaphragm according to the invention shown by itself.

As shown by the overhead view visible in FIG. 6, each petal has a contour with an overall shape of an isosceles triangle, the apex angle of the two main sides, i.e. of the longest sides of identical length, whereof is equal to thirty degrees in the example shown in the figures, that is to say when there are twelve petals.

Figure 5:
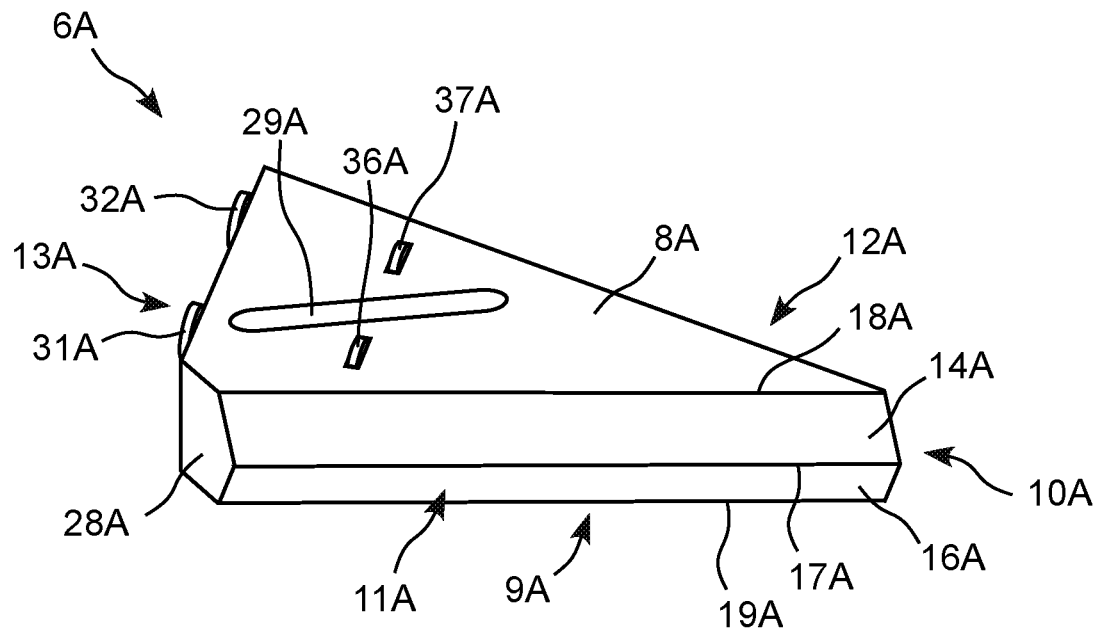
FIG. 5 is a first perspective view of a petal of the diaphragm according to the invention shown by itself.

As shown in FIGS. 5 and 6, the petal 6A, which is identical to the others, includes a top face 8A parallel to a bottom face 9A, while being delimited by a first, a second and a third edge 11A, 12A, 13A. The distance between the top face and the bottom face is constant and corresponds to the thickness of the petal.

The first and the second edges 11A, 12A have the same length measured parallel to the top and bottom faces, whereas the third edge 13A, corresponding to the base of the triangle, is much shorter, whereby the angle formed by the edges 11A and 12A being thirty degrees when viewed perpendicularly to the faces 8A and 9A. The junction between the edges 11A and 12A corresponds to the acute apex 10A of the petal 6A.

The third edge 13A is flat and oriented perpendicularly to the faces 8A and 9A, whereas the first edge 11A has a domed shape, in other words a convex shape, and whereas the second edge 12A has a complementary hollow shape, in other words a concave shape.

More particularly, the first edge 11A is formed by two rectangular flat facets 14A and 16A inclined relative to one another, and which come together halfway between the top face 8A and the bottom face 9A so as to delimit a projecting central ridge 17A oriented parallel to the faces 8A and 9A.

The facet 14A delimits, with the top face 8A, a top ridge 18A, and the facet 16A delimits with the bottom face 9A a bottom ridge 19A. The ridges 17A, 18A and 19A are parallel to one another, as shown in FIG. 5.

Similarly, the second edge 12A is formed by two rectangular flat facets 21A and 22A delimiting therebetween and with the top face 8A and the bottom face 9A three ridges 23A, 24A, 26A parallel to one another. However, the facets 21A and 22A are inclined relative to one another by a reentrant angle so as to give the second edge 12A a hollow shape that complements that of the first edge 11A.

Figure 7:
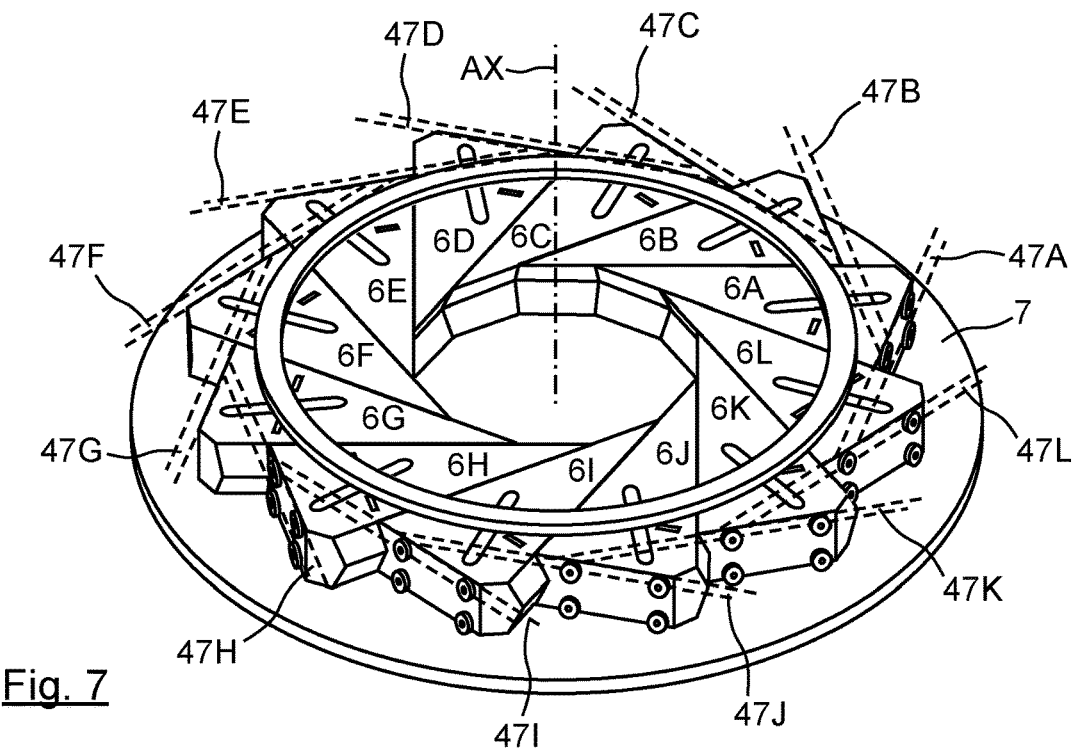
FIG. 7 is a perspective view of the diaphragm according to the invention without the cover thereof and partially open, showing the arrangement of the guideways thereof.

Optionally and as shown in FIGS. 6 and 7, the junction between the first edge 11A and the third edge 13A is constituted by a bevelled apex 28A delimiting a flat face of intermediate orientation relative to the first edge and to the third edge, and which is perpendicular to the faces 8A and 9A.

Figure 8:
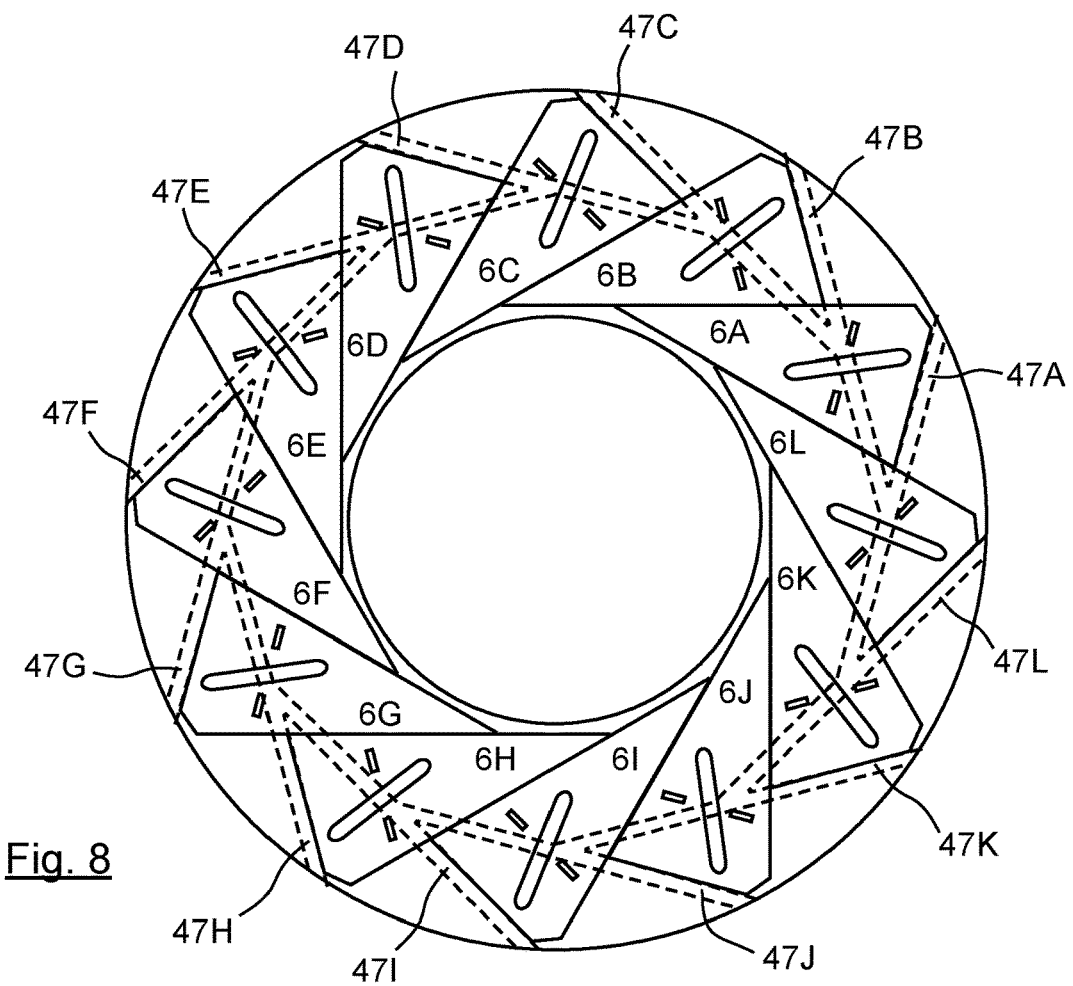
FIG. 8 is an overhead view of the diaphragm according to the invention without the cover thereof and maximally open, showing the arrangement of the guideways thereof.

This bevel 28A allows the external overall dimensions of the diaphragm to be reduced when at the maximum opening thereof. In this situation, which is shown in FIG. 8, the bevel of each petal constitutes the closest portion to the outer periphery of the base, such that it allows the radial span of each petal to be reduced, which allows the outer diameter of the base and of the cover to be reduced, and thus the outer diameter of the entire diaphragm.

As shown in FIGS. 5 and 6, this petal 6A includes a rectilinear groove 29A opening out into the top face thereof. This groove 29A extends from the vicinity of the third edge 13A as far as substantially halfway along the length of the petal in a region in the vicinity of the second edge 12A. It has an overall orientation that is close to that of the first edge, while forming a slight angle relative to the orientation of this first edge.

The third edge 13A supports four ball bearings, denoted by the reference numerals 31A, 32A, 33A, 34A which limit friction caused when the petal is displaced relative to the base of the diaphragm.

The ball bearings are supported by the third edge 13A so as to rotate about axes perpendicular to the flat face and perpendicular to the faces 8A and 9A constituted by this third edge 13A. The rotational axes of these bearings are disposed at the apexes of a rectangle extending within the rectangular face forming the third edge 13A.

The ball bearings 31A and 32A slightly protrude from the top face 8A, and similarly, the ball bearings 33A and 34A protrude from the bottom face 9A.

In a complementary manner, the petal 6A is equipped with four other ball bearings, two of these other bearings denoted by the reference numerals 36A and 37A being visible in the figures since they are flush with the top face 8A. These two bearings 36A and 37A, which also rotate about axes perpendicular to the flat face constituting the third edge 13A, are located on either side of the groove 29A, substantially halfway along the length of this groove.

The other two bearings not visible in FIGS. 5 and 6 are disposed in a symmetric manner so as to be flush with the bottom face 9A, perpendicular to the bearings 36A and 37A.

The twelve petals are all identical to the petal 6A, and when the diaphragm is completely closed, as shown in FIGS. 1 and 3, they are arranged on the base 7 in the form of a rosette about the axis AX, the acute apex of each petal thus being coincident with the axis AX. Adjacent petals are spaced thirty degrees apart about the axis AX.

In this configuration, the first edge 11A of the petal 6A extends along the second edge 12A of the petal 6B, while being interlocked inside one another, the edge 11A having a raised profile interlocking inside the complementary hollow profile of the second edge of the petal 6B. The second edge of the petal 6A extends along the first edge of the petal 6L, and these two edges are interlocked inside one another in the same way.

Thus, the edges of adjacent petals extend alongside one another while being substantially interlocked, the assembly forming a continuous wall constituting an obstacle to ionising radiation. Thanks to the interlocking of the edges procured by the complementary profiles thereof, radiation cannot pass through the small gap separating two edges that extend alongside one another, since the path formed by this gap is not rectilinear, but instead is angulous.

When the diaphragm is partially or completely open, the adjacent edges of the different petals still bear against one another and are interlocked with one another, which forms an obstacle for the passage of radiation outside of the central opening thus delimited by this diaphragm.

The opening of the diaphragm is obtained by the translational displacement of each petal parallel to the third edge thereof so as to move the acute apex thereof away from the major axis, while ensuring that the edges of the different adjacent petals remain joined, which is in particular shown in FIG. 4.

This opening movement is procured by pivoting a manoeuvring wheel, denoted by the reference numeral 38 in the figures, which includes a bearing face pressed against the top faces of the different petals, and which is centred about the axis AX while fully extending around and outside of the central opening 4 of the cover.

This wheel 38 includes, at the bearing face thereof, a series of twelve drive fingers 39A-39L spaced thirty degrees apart from one another, and each of which is engaged inside the rectilinear groove 29A-29L of a corresponding petal. The locations of these fingers are shown symbolically by way of broken lines in FIGS. 3 and 4, and are identified in FIG. 4 with the corresponding grooves.

This wheel 38 is guided in rotation about the axis AX by sliding within a circular groove, not shown, which is formed at the bottom face of the wall 3 of the cover 2. In other words, the wheel 38 is imprisoned between the wall of the cover 2 and the top faces of the petals, while only being free to rotate within the circular groove of the cover in which it is housed.

In a complementary manner, this wheel 38 includes two manoeuvring studs 42 and 43 protruding from the top face thereof and being spaced one hundred and eighty degrees apart from one another about the axis AX, i.e. symmetrical to one another relative to the axis AX. These studs 42 and 43 pass through the top wall 3 of the cover 2 through two arched slots 44 and 46 formed in the cover and which are also disposed one hundred and eighty degrees apart from one another about the axis AX such that they are symmetrical to one another relative to this axis, as shown in FIGS. 1 and 2.

An operator can thus handle these studs in order to pivot the wheel 38 in the receptacle thereof about the axis AX in order to manoeuvre the diaphragm by jointly and simultaneously displacing the twelve petals so as to move them away from or closer to the axis AX.

Each petal is guided in translation such that it can only be displaced parallel to the third side thereof, such that a rotation of the wheel 38 allows, thanks to each of the fingers 39A-39L connected to a petal, these petals to undergo translational displacement, each in the direction specific thereto in order to open or close the diaphragm according to the direction of rotation of the wheel 38.

In the arrangement shown in the figures, a rotation of the wheel 38 in the forward direction causes the diaphragm to open, whereas a rotation in the reverse direction causes the diaphragm to close.

The translational guidance of the different petals is procured by the ball bearings guided in the corresponding guideways, formed at the bottom face of the wall 3 of the cover, and which are shown by broken lines in FIGS. 7 and 8. Each of these guideways, denoted by the reference numerals 47A to 47L extend in the direction of the third edge of the petal 6A-6L guided thereby.

More particularly, the guideway 47A extends in the direction of the edge 13A of the petal 6A, and it receives the ball bearings 31A and 32A of this petal in order to form the bearing track thereof by guiding them. The petal 6A is thus only capable of moving in translation in the direction of the guideway 47A. In the same way, each petal is guided by a corresponding guideway, receiving the two ball bearings supported by the third edge thereof, and which are flush with the top face thereof.

As shown in FIGS. 7 and 8, adjacent guideways are inclined relative to one another by thirty degrees, in the same way that the adjacent petals also form angles of thirty degrees relative to one another.

In a tangible manner, each petal is capable of moving in translation in a direction forming a certain angle relative to this petal, and this angle is identical for each petal. In the example shown in the figures, each petal is capable of moving in a direction that is coincident with the orientation of the third edge thereof.

Each guideway is, for example, formed by milling the bottom face of the wall 3.

Similarly, another set of twelve guideways is formed at the top face of the base 7, according to the same arrangement, i.e. perpendicularly to the guideways formed in the wall 3.

The entire diaphragm according to the invention is easy to dismantle and assemble. The mounting thereof firstly consists of fastening the base around the sheath to be equipped, for example by means of a plurality of screws passing therethrough. Once this operation is complete, the petals are positioned on the base, for example in the closed configuration, before placing the wheel 38 on the top faces of the petals, in order to then mount the cover 2 onto this assembly.

The rigid connection of the cover 2 with the base is ensured by three screws 48, 49, 51 which pass through the top wall 3 of the cover in order to be screwed into the base, these three screws being disposed at one hundred and twenty degrees about the axis AX, while being oriented parallel to this axis AX.

In the example shown in FIGS. 2, 4 and 7, the diaphragm is partially open. When it is maximally open, as shown in FIG. 8, the opening procured by the petal has a diameter that corresponds to the central opening 4 of the cover, the base 7 comprising an identical central opening that is visible in FIG. 8.

The possibility of only partially opening the diaphragm allows for the use of any range of poles having diameters that are less than that of the central opening 4.

In the example shown in the figures, the diaphragm includes twelve petals; however, this number can be modified. In a tangible manner, the central opening of the diaphragm is increasingly circular as the number of petals is increased. In an extreme manner, a diaphragm including four petals capable of moving in translation would procure a square-shaped central opening, while operating in a manner similar to that shown by the figures.

In general, the invention provides a biological protection that adapts to tools, poles or other equipment with an entire range of diameters, while limiting the assembly and removal operations during interventions, and while allowing the site to be switched over to safety mode in a fast and complete manner after an intervention, by fully obstructing the sheath. This protection can be mounted on a horizontal plane or on a vertical plane.

In the first embodiment, which is shown in FIG. 1 to 8, the protection according to the invention includes a single diaphragm providing protection from radiation.

Figure 9:
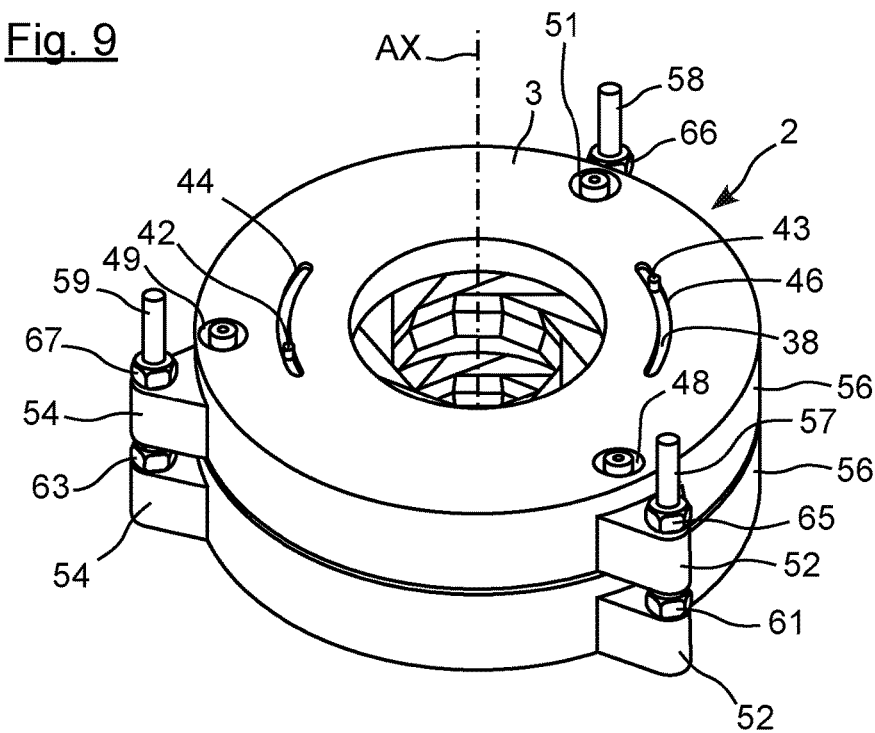
FIG. 9 is a perspective view of a second embodiment of the invention including two diaphragms mounted one on top of the other.
Figure 10:
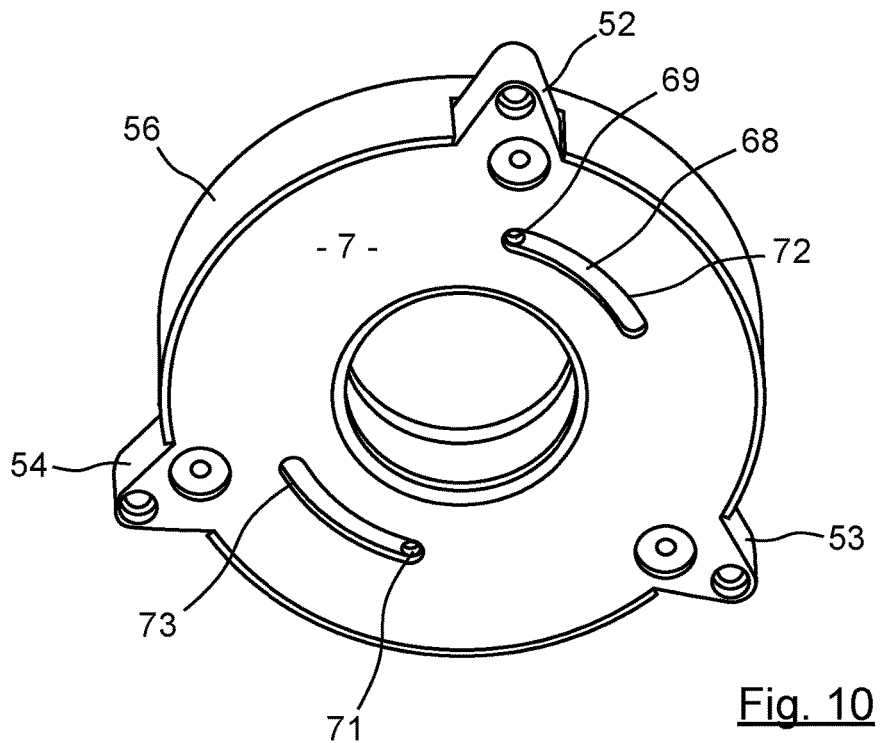
FIG. 10 is a perspective view showing a bottom face of the diaphragm according to the second embodiment.
Figure 11:
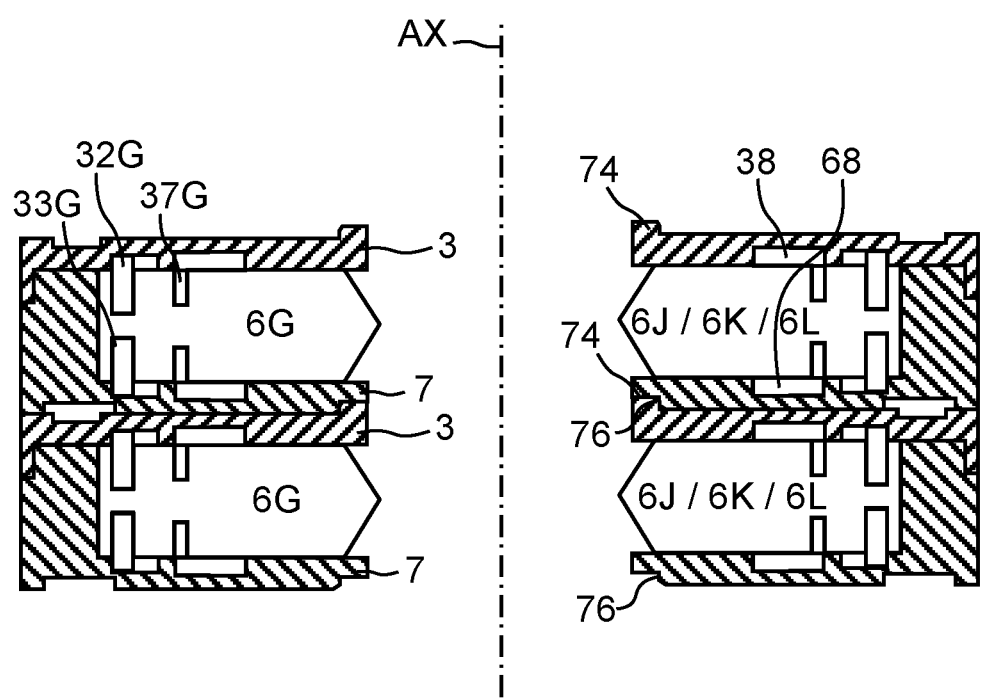
FIG. 11 is a sectional view of two diaphragms mounted one on top of the other according to the second embodiment.

In a second embodiment, the protection includes two diaphragms coaxially mounted on top of one another, as shown in FIG. 9 to 11, in order to increase the thickness of the protection and/or reduce the mass of each diaphragm that must be handled for the installation. A diaphragm is thus mounted on top of another diaphragm, in a coaxial manner, in order to delimit two central openings superimposed on top of one another, which are jointly manoeuvred with the manoeuvring wheel of the mounted diaphragm.

In this second embodiment, the diaphragm also includes a base supporting petals receiving a rotary manoeuvring wheel, being closed by a cover provided with arched slots allowing this manoeuvring wheel to be actuated, according to an arrangement that is very similar to the diaphragm in FIG. 1 to 8.

As shown in FIG. 10, the base 7 is provided with three lugs 52, 53, 54 which radially project from the cover 2 by radially passing through the cylindrical side wall 56 extending from the top wall 3 of this cover. For this purpose, this cylindrical wall 56 includes three notches for the passage of the lugs. The lugs 52-54 described here for the second embodiment can also be provided within the scope of the diaphragm described with reference to FIG. 1 to 8.

The lugs 52-54 are located at 120° from one another about the axis AX, and a fastening hole oriented parallel to the axis AX passes through each thereof. The fastening of the first diaphragm is ensured by means of three threaded rods 57-59 screwed into the wall to be equipped, about the opening in this wall, while being oriented perpendicularly to this wall, before engaging the lugs 52-54 on these rods 57-59 until the base of the diaphragm is pressed against the wall. Nuts 61-63 are screwed onto the rods 57-59, then clamped onto the lugs 52-54 in order to effectively press the diaphragm onto the wall supporting it.

The second diaphragm is thus engaged on the threaded rods 57-59 in order to press it onto the first diaphragm, before screwing three other nuts 65-67 onto the rods 57-59 in order to clamp them onto the lugs so as to press this mounted diaphragm onto the diaphragm supported by the wall.

In this second embodiment, the mounted diaphragm includes, in addition to the manoeuvring wheel 38 thereof, a transmission wheel 68 allowing the movement of the manoeuvring wheel 38 thereof to be transferred to the manoeuvring wheel of the diaphragm onto which it is mounted.

This transmission wheel 68 is similar to the manoeuvring wheel 38, except in that it extends along the base 7 instead of along the cover 2, and in that it is driven by the petals moved by the manoeuvring wheel 38 instead of being directly manoeuvred by an operator.

This wheel 68 includes drive fingers, not shown, preferably two fingers that are symmetrical to one another relative to the axis AX, and each of which is engaged in a bottom rectilinear groove of a corresponding petal. These bottom rectilinear grooves, not shown, are formed at the bottom faces of each petal, perpendicular to the grooves 29A-29L formed at the top faces thereof.

This wheel 68 is guided in rotation about the axis AX by sliding within a circular groove, formed at the top face of the base 7 supporting it: it is imprisoned between the wall of the base 7 and the bottom faces of the petals, while only being free to rotate about the axis AX.

When the petals are displaced by pivoting the manoeuvring wheel 38 about a given angle, the transmission wheel 68 thus pivots about the same angle by being displaced by the petals.

This transmission wheel 68 includes two holes 69 and 71 at the bottom face thereof, which are symmetrical to one another relative to the axis AX. These holes can be accessed via two arched slots 72 and 73 formed in the base 7 and disposed symmetrically relative to the axis AX, as shown in FIG. 10.

When a diaphragm is mounted on a diaphragm already present, as shown in FIG. 10, the studs 42 and 43 of the manoeuvring wheel 38 of the diaphragm already present engage inside the holes 69, 71 of the transmission wheel 68 of the mounted diaphragm, through the arched slots 72, 73. Once the assembly is in place, a given angular displacement of the manoeuvring wheel of the mounted diaphragm causes the transmission wheel thereof to undergo the same displacement, and the manoeuvring wheel of the diaphragm already present to undergo the same displacement.

Thus, when the manoeuvring wheel of the mounted diaphragm is rotationally displaced in order to open the mounted diaphragm, this displacement causes the same opening of the diaphragm already present.

The transmission wheel 68 thus allows the openings of the two diaphragms mounted on top of one another to be synchronised such that only one manoeuvring wheel must be actuated in order to open the two diaphragms to a given degree of opening or to close the two diaphragms.

As shown in FIG. 11, the cover advantageously includes a circumferential edge 74 surrounding the central opening 4 thereof and projecting from the top face thereof in order to interlock inside a corresponding shoulder 76 formed at the bottom face of the base 7 at the central opening of this base 7.

When stacking one diaphragm on top of another diaphragm already in place, the circumferential edge 74 of the diaphragm already in place interlocks inside the shoulder 76 of the mounted diaphragm so as to ensure accurate centring of the two diaphragms relative to one another, these diaphragms thus being interlocked on top of one another.

The invention claimed is:

1. Biological protection for closing an opening in a containment wall of a radioactive zone, this protection comprising an iris-type diaphragm including a base in the form of a flat disc directly supporting a contact surface of petals, the petals being formed by flat plates having substantially triangular contours and made of at least one material protecting from ionising radiation, which petals are capable of being displaced parallel to the base between an open state in which these petals jointly delimit a central opening and a closed state in which these petals are brought together to jointly form a continuous closed wall, wherein each petal comprises ball bearings in order to limit the friction forces generated between the petals and the base during the displacement of these petals, wherein at least one of the ball bearings comprises the contact surface.

2. Biological protection according to claim 1, wherein the ball bearings comprise means for guiding in translation each petal relative to the base, each petal being guided in a direction of translational displacement that is specific thereto, each direction of displacement of a petal forming a certain angle relative to this petal, this angle being identical for each petal.

3. Biological protection according to claim 2, including a cover, wherein the guide means are constituted by guideways formed in the cover and/or in the base, each guideway constituting a bearing track receiving one or more ball bearings of the petal guided thereby.

4. Biological protection according to claim 1, including a cover having a central opening, this cover covering all or part of the petals while being fastened to the base.

5. Biological protection according to claim 4, including a manoeuvring wheel mounted such that it can rotate relative to the cover and including, for each petal, a drive finger engaging within a corresponding groove of the corresponding petal in order to jointly displace all of the petals by rotating the wheel.

6. Biological protection according to claim 5, wherein the wheel includes at least one manoeuvring stud passing through an arched slot formed in the cover, allowing this wheel to be rotated by displacing the stud along this slot in order to manoeuvre the protection between the open state thereof and the closed state thereof.

7. Biological protection according to claim 5, including a transmission wheel mounted such that it can rotate relative to the base and including a plurality of drive fingers, each engaging within a groove of a corresponding petal, this transmission wheel including at least one transmission hole capable of receiving a drive stud of a manoeuvring wheel of another protection on which this protection is mounted, through at least one arched slot formed in the base.

8. Biological protection system including: a first protection comprising an iris-type diaphragm including a base in the form of a flat disc directly supporting petals formed by flat plates having substantially triangular contours and made of at least one material protecting from ionising radiation, which petals are capable of being displaced parallel to the base between an open state in which these petals jointly delimit a central opening and a closed state in which these petals are brought together to jointly form a continuous closed wall; and at least one second protection according to claim 7, the at least one second protection being mounted on top of the first protection.

9. Biological protection according to claim 1, including a cover, wherein each petal supports ball bearings in order to limit the friction forces generated between the petals and the cover during the displacement of these petals.

10. Biological protection according to claim 1, wherein the different petals are identical, each petal having a substantially triangular shape, comprising a first edge and a second edge, and wherein all of the adjacent petals extend alongside one another by the first and second respective edges thereof, for any opening position of the diaphragm.

11. Biological protection according to claim 10, wherein the first edge has a domed profile and the second edge of each petal has a hollow profile that complements the profile of the first edge.

12. Biological protection according to claim 1, wherein each petal has a substantially triangular contour having a bevelled apex, in order to limit the external overall dimensions of the protection in a maximally-open state.

* * * * *